(12) United States Patent
Fusco et al.

(10) Patent No.: US 10,045,976 B2
(45) Date of Patent: Aug. 14, 2018

(54) NICOTINE-CONTAINING LIQUID FORMULATIONS AND USES THEREOF

(71) Applicant: Euro-Pharm International Canada Inc., Montreal, Quebec (CA)

(72) Inventors: Rolando Fusco, Montreal (CA); Leonardo Calderone, Montreal (CA)

(73) Assignee: EURO-PHARM INTERNATIONAL CANADA INC., Montreal, Quebec (CA)

(\*) Notice: Subject to any disclaimer, the term of this patent is extended or adjusted under 35 U.S.C. 154(b) by 0 days.

(21) Appl. No.: 15/366,678

(22) Filed: Dec. 1, 2016

(65) Prior Publication Data

US 2017/0157107 A1    Jun. 8, 2017

(30) Foreign Application Priority Data

Dec. 3, 2015    (CA) ..................................... 2914089

(51) Int. Cl.
  *A61K 31/465*    (2006.01)
  *A61K 9/00*    (2006.01)
  *A61K 47/26*    (2006.01)
  *A61K 47/10*    (2017.01)

(52) U.S. Cl.
  CPC ............ *A61K 31/465* (2013.01); *A61K 9/006* (2013.01); *A61K 47/10* (2013.01); *A61K 47/26* (2013.01)

(58) Field of Classification Search
  USPC .......................................................... 514/343
  See application file for complete search history.

(56) References Cited

U.S. PATENT DOCUMENTS

| | | |
|---|---|---|
| 2004/0002520 A1 | 1/2004 | Soderlund et al. |
| 2007/0163610 A1 | 7/2007 | Lindell et al. |
| 2009/0023819 A1 | 1/2009 | Axelsson |
| 2010/0063111 A1 | 3/2010 | Lindell et al. |
| 2011/0293535 A1 | 12/2011 | Kosik et al. |
| 2015/0230515 A1* | 8/2015 | Lampe .................. A24B 13/00 131/310 |

OTHER PUBLICATIONS

Nicotrol® NS, Pfizer (Pharmacia & Upjohn Co), Jan. 2010.
Product information, Nicorette® Quickmist, mouth spray—1mg/spray, Oct. 13, 2014.

* cited by examiner

*Primary Examiner* — Jeffrey S Lundgren
*Assistant Examiner* — Michael J Schmitt
(74) *Attorney, Agent, or Firm* — Edward J. Baba; Bozicevic, Field & Francis LLP

(57) ABSTRACT

Nicotine liquid formulations and their use in therapy, for instance, in nicotine replacement therapy are described. More specifically, the technology relates to liquid nicotine formulations comprising nicotine, one or more diol and/or triol, and a sugar alcohol, which may be used as sprays for administration through the oral cavity, such as the palate.

21 Claims, No Drawings

NICOTINE-CONTAINING LIQUID FORMULATIONS AND USES THEREOF

TECHNICAL FIELD

The technology generally relates to nicotine formulations and their use in therapy, for instance, in nicotine replacement therapy. More specifically, the technology relates to liquid nicotine formulations, which may be used as sprays for administration through the oral cavity.

BACKGROUND

Nicotine is an alkaloid present in plants of the Solanaceae family like the tobacco plant. Apart from nicotine, tobacco leaves also include a complex mixture of compounds which, when burned and inhaled, are associated with serious health conditions, including heart diseases and lung cancer. The role of nicotine in the addiction to tobacco has now been recognized for a few decades.

However, even though the majority of users intend to stop smoking at one point or another, they are all faced with symptoms of withdrawal such as cravings, irritability, weight gain and/or depression when attempting to quit. One treatment to help reduce withdrawal symptoms includes the administration of medication, such as antidepressants or other compounds like varenicline or clonidine, all of which may present secondary effects to various degrees. For instance, the monitoring of patients using antidepressants by a medical professional on a regular basis is highly recommended to promptly identify any adverse effects.

Another approach to reduce withdrawal symptoms consists in what is called nicotine replacement therapy (NRT). In NRT, nicotine is delivered in a form which avoids risks associated with smoking, for instance, transdermally or through the mouth cavity. For instance, NRTs include nicotine patches, gums, mouth and nasal sprays, inhalers, tablets and lozenges. NRTs may also be combined together or with other smoking cessation aids such as medication or counselling.

Among NRTs, nicotine sprays are generally presented as aqueous solutions provided in a bottle which delivers metered doses to the mouth cavity. Absorption of the active is achieved through the oral mucosa. However, nicotine sprays usually also include ethanol, which even in small quantities, may not be suited for all users. Additionally, a burning sensation is often reported by spray users, which could lead to treatment interruption and relapse of the patient. A quicker absorption could also benefit patients in helping to reduce symptoms more spontaneously. There is a need for new formulations which will suit the need of certain populations of users, for instance, being alcohol free, having enhanced absorption and/or having a reduced burning sensation.

SUMMARY

According to one aspect, the present application relates to a liquid formulation comprising nicotine, at least one lower alkyl diol and/or triol, a sugar alcohol and water. According to at least one embodiment, the liquid formulation is free of ethanol.

In one embodiment, the content in nicotine in the formulation ranges from about 0.2 wt % to about 2.5 wt %, for instance, from about 0.4 wt % to about 1.5 wt %. For instance, the formulation is adapted to deliver an amount of about 1 mg or about 2 mg.

According to another embodiment, the sugar alcohol present in the formulation is selected from maltitol, sorbitol, xylitol, erythritol, and isomalt, for instance the sugar alcohol is xylitol. In one embodiment, the content in sugar alcohol in the formulation ranges from about 0.5 w % to about 10 wt %, for instance from about 0.8 w % to about 5 wt %. In another embodiment, the weight ratio of sugar alcohol to nicotine is within the range of about 1:1 to about 3:1, preferably about 2:1.

In a further embodiment, the formulation comprises two or more lower alkyl diol, lower alkyl triol, or a combination thereof. In one embodiment, the lower alkyl diol and/or triol in the formulation is selected from ethylene glycol, propylene glycol, and glycerol. In another embodiment, the total content in lower alkyl diol and/or triol in the formulation ranges from about 45 wt % to about 85 wt %, or from about 55 wt % to about 75 wt %.

In one embodiment, the lower alkyl diol and/or triol in the formulation comprises both propylene glycol and glycerol, for instance, in a weight ratio of about 4:6 to about 8:2.

In another embodiment, the formulation further comprises a flavoring agent, for instance selected from mint, grape, orange, coffee, and combinations thereof. In an embodiment, the content in flavoring agent in the formulation is from about 3 wt % to about 20 wt %.

In yet another embodiment, the content in water in the formulation is lower than 30 wt %, for example within the range of about 10 wt % to about 25 wt %.

The application also further relates to the use of a formulation as herein defined for treating, reducing, and/or alleviating at least one tobacco withdrawal symptom, and to methods of treating, reducing, and/or alleviating at least one tobacco withdrawal symptom in a subject in need thereof, comprising administering an effective amount of a liquid formulation as herein defined. The formulation as herein defined in a form suited for administration to the mouth cavity (such as the palate), for instance, in the form of an oral spray.

DETAILED DESCRIPTION

All technical and scientific terms used herein have the same meaning as commonly understood by one ordinary skilled in the art to which the present technology pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a diol" also contemplates a mixture of two or more diols. It should also be noted that the term "or" is generally employed in its sense including "and/or" unless the content clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of ±20%, or ±10% of a given value. Where particular values are described in the application and claims, unless otherwise stated the term "about" meaning within an acceptable error range for the particular value should be assumed.

The term "nicotine" refers both to the free base of nicotine as well as to pharmaceutically acceptable salts or derivatives of nicotine. Pharmaceutically acceptable salts refer to salts of nicotine which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977), incorporated herein by reference in its entirety and for all purposes. A "pharmaceutically acceptable derivative" includes any non-toxic prodrug, conjugate, complex, or other derivative of nicotine that, upon administration to a subject, is capable of providing nicotine, either directly or indirectly.

The expressions "lower diol and/or triol", "lower alkyl diol and/or triol" and equivalents refer to a lower alkyl molecule having from 2 to 4 carbons (i.e. a C2-C4alkyl), and having two or three hydroxyl groups respectively per molecule. The expression is meant to include a single compound or a mixture of two or more compounds.

The expression "sugar alcohol" designates an alcohol which is a reduced form of the aldehyde group present in its corresponding sugar molecule. Examples of sugar alcohols include, without limitation, maltitol, sorbitol, xylitol, erythritol, isomalt, and combinations thereof.

The expression "flavoring agents" as used herein, designates natural or synthetic agents which provide an appealing taste to the formulation, masks the taste of nicotine and/or excipients, and/or help in reducing the burning sensation associated with nicotine liquid formulations when administered through the mouth cavity. Examples of flavoring agents include, without limitations, mint, spearmint, pepper mint, wintergreen, menthol, eucalyptus, cinnamon, cocoa, vanilla, aniseeds, liquorice, fruit flavor (e.g. grape, cherry, strawberry, raspberry, melon, banana, papaya, mango, peach, pineapple, cranberry, apple, orange, lemon, lime, etc.), coffee, tea, tobacco flavor, artificial or natural brew and liquor flavors, and the like, or a combination thereof.

The liquid formulations as herein defined preferably include nicotine in any form, at least one lower alkyl diol and/or triol, a sugar alcohol, a flavoring agent and water, for instance, in an amount which is lower than the amount of lower alkyl diols and/or triols within the formulation. In some examples, the liquid formulation is free of ethanol.

Nicotine is preferably present in the formulation in an amount which ranges from about 0.2 wt % to about 2.5 wt %, for instance from about 0.4 wt % to about 1.5 wt %. For example, nicotine is present in the formulation at a concentration which is adapted to deliver a dose of about 1 mg or about 2 mg, for instance, in one spray dose.

For example, the sugar alcohol present in the formulation is selected from maltitol, sorbitol, xylitol, erythritol, and isomalt, preferably the sugar alcohol is xylitol. In one embodiment, the content in sugar alcohol in the formulation ranges from about 0.5 w % to about 10 wt %, for instance from about 0.8 w % to about 5 wt %. Preferably, the weight ratio of sugar alcohol (e.g. xylitol) to nicotine is within the range of about 1:1 to about 3:1, for example, about 2:1.

The formulation also comprises at least one, preferably two, lower alkyl diol, lower alkyl triol, or a combination thereof. For instance, the lower alkyl diol and/or triol in the formulation is selected from ethylene glycol, propylene glycol, and glycerol. In another embodiment, the total content in lower alkyl diol and/or triol in the formulation ranges from about 45 wt % to about 85 wt %, or from about 55 wt % to about 75 wt %. In one example, the lower alkyl diol and/or triol in the formulation comprises both propylene glycol and glycerol, for instance, in a weight ratio of about 4:6 to about 8:2.

The formulation further comprises a flavoring agent, for instance selected from mint, grape, orange, coffee, or a combination thereof. In one example, the content in flavoring agent in the formulation is from about 3 wt % to about 20 wt %.

The liquid formulation comprises water, for instance, in an amount which is lower than 30 wt %, or within the range of about 10 wt % to about 25 wt %.

Additional excipients may also be present in the liquid formulation in minor amounts, including antibacterial agents, preservatives, buffers, etc. The liquid formulation is included in a container like a spray bottle for administration. Such container may further include a propulsion gas acceptable for human use.

The recitation of an embodiment herein includes that embodiment as any single embodiment or in combination with any other embodiments described herein or portions thereof.

One example of a liquid formulation of the present application includes:
  nicotine at 0.2 wt % to 2.5 wt %;
  a sugar alcohol (e.g. xylitol) in a weight ratio of about 1:1 to about 3:1 v. nicotine;
  a lower alkyl diol and/or triol, at a total content of 45 wt % to 85 wt %;
  water in an amount of 30 wt % or less; and
  a flavoring agent at 3 wt % to 20 wt %.

In another example, the liquid formulation comprises:
  nicotine at 0.2 wt % to 2.5 wt %;
  a sugar alcohol (e.g. xylitol) in a weight ratio of about 1:1 to about 3:1 v. nicotine;
  a lower alkyl diol and/or triol, at a total content of 55 wt % to 75 wt %;
  water in an amount of 30 wt % or less; and
  a flavoring agent at 3 wt % to 20 wt %.

In another example, the liquid formulation comprises:
  nicotine at 0.2 wt % to 2.5 wt %;
  a sugar alcohol (e.g. xylitol) in a weight ratio of about 1:1 to about 3:1 v. nicotine;
  a lower alkyl diol and/or triol, at a total content of 55 wt % to 75 wt %, comprising propylene glycol and glycerol in a weight ratio of about 4:6 to about 8:2;
  water in an amount of 30 wt % or less; and
  a flavoring agent at 3 wt % to 20 wt %.

In yet another example, the liquid formulation comprises:
  nicotine at 0.4 wt % to 1.5 wt %;
  a sugar alcohol (e.g. xylitol) in a weight ratio of about 1:1 to about 3:1 v. nicotine;
  a lower alkyl diol and/or triol, at a total content of 45 wt % to 85 wt %;
  water in an amount of 30 wt % or less; and a flavoring agent at 3 wt % to 20 wt %.

In a further example, the liquid formulation comprises:
nicotine at 0.4 wt % to 1.5 wt %;
a sugar alcohol (e.g. xylitol) in a weight ratio of about 1:1 to about 3:1 v. nicotine;
a lower alkyl diol and/or triol, at a total content of 55 wt % to 75 wt %;
water in an amount of 30 wt % or less; and
a flavoring agent at 3 wt % to 20 wt %.

In a further example, the liquid formulation comprises:
nicotine at 0.4 wt % to 1.5 wt %;
a sugar alcohol (e.g. xylitol) in a weight ratio of about 1:1 to about 3:1 v. nicotine;
a lower alkyl diol and/or triol, at a total content of 55 wt % to 75 wt %, comprising propylene glycol and glycerol in a weight ratio of about 4:6 to about 8:2;
water in an amount of 30 wt % or less; and
a flavoring agent at 3 wt % to 20 wt %.

In a further example, the liquid formulation comprises:
nicotine at 0.4 wt % to 1.5 wt %;
xylitol in a weight ratio of about 1:1 to about 3:1 v. nicotine;
a lower alkyl diol and/or triol, at a total content of 55 wt % to 75 wt %;
water in an amount of 30 wt % or less; and
a flavoring agent at 3 wt % to 20 wt %.

In a further example, the liquid formulation comprises:
nicotine at 0.4 wt % to 1.5 wt %;
xylitol in a weight ratio of about 1:1 to about 3:1 v. nicotine;
a lower alkyl diol and/or triol, at a total content of 55 wt % to 75 wt %, comprising propylene glycol and glycerol in a weight ratio of about 4:6 to about 8:2;
water in an amount of 30 wt % or less; and
a flavoring agent at 3 wt % to 20 wt %.

In a further example, the liquid formulation comprises:
nicotine at 0.4 wt % to 1.5 wt %;
xylitol in a weight ratio of about 2:1 v. nicotine;
a lower alkyl diol and/or triol, at a total content of 55 wt % to 75 wt %;
water in an amount of 30 wt % or less; and
a flavoring agent at 3 wt % to 20 wt %.

In a further example, the liquid formulation comprises:
nicotine at 0.4 wt % to 1.5 wt %;
xylitol in a weight ratio of about 2:1 v. nicotine;
a lower alkyl diol and/or triol, at a total content of 55 wt % to 75 wt %, comprising propylene glycol and glycerol in a weight ratio of about 4:6 to about 8:2;
water in an amount of 30 wt % or less; and
a flavoring agent at 3 wt % to 20 wt %.

In any one of the above examples, the water content in the liquid formulation may also be within the range of 10 wt % to 25 wt %.

An "effective amount" of the liquid formulation as herein described includes an amount of nicotine that will elicit the biological or medical response in a subject that is being sought. For example, an effective amount is defined as amount which would, as compared to a corresponding subject who has not received such amount, result in treatment, prevention, reduction or alleviation of at least one symptom of nicotine withdrawal. Nicotine withdrawal symptoms include cravings (urges to use tobacco), anxiety, irritability, depression, and weight gain. For instance, an amount per spray dose (i.e. delivered in 1 push of a spray bottle) may be about 1 mg or about 2 mg.

As used herein, the terms "treatment," "treat," and "treating" refer to alleviating, delaying the onset of, or reducing at least one symptom associated with nicotine withdrawal, as described herein. In some embodiments, treatment may be administered after one or more symptoms have developed. In other embodiments, treatment may be administered to a susceptible individual prior to the onset of symptoms. For instance, the product is used at the moment a nicotine craving develops and this nicotine craving needs to be suppressed. That way, instead of using a tobacco product, the individual being treated may take one or two spay dose(s) of the liquid formulation to remove, alleviate or delay the immediate requirement for nicotine.

The term "subject" as used herein refers to a subject susceptible of encountering nicotine withdrawal symptoms, for instance, a human subject who has been exposed to nicotine for a period of time, e.g. a human who has been smoking tobacco products for instance for at least 2 months, or at least 6 months, or at least 1 year, and for whom exposition is stopped or substantially reduced (e.g. a subject quitting smoking).

It should also be understood that the dose, daily dosage and/or frequency of administration for any particular subject will depend upon a variety of factors, including age, body weight, general health, time of administration, drug combination, the frequency and duration of previous exposure to nicotine (e.g. smoking habits), the judgment of the treating physician, and the frequency and severity of nicotine withdrawal symptoms. For instance, one or two spray dose(s) may be administered on an "as needed" basis or as determined by a medical professional. The total daily usage may not exceed the amount recommended by local health authorities. The present liquid formulation may also be used in combination or coincidental with other NRT(s) (e.g. patches, lozenges, gums), tobacco cessation drugs, and/or behavioral counseling, given that combination of the formulation with other NRT(s) is allowed and accepted by health authorities and that the total daily dose of nicotine absorbed by the subject is at or below the limit accepted by such authorities.

The Example set forth herein below provide an example of production of a formulation as defined herein. Unless otherwise indicated, all numbers expressing quantities of ingredients, conditions, concentrations, and so forth used in the specification and claims are to be understood as being modified in all instances by the term "about." At the very least, each numerical parameter should at least be construed in light of the number of significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The following is to be construed as merely illustrative, and not limitations of the preceding disclosure in any way whatsoever. Those skilled in the art will promptly recognize appropriate variations from the procedures both as to ingredients and as to conditions and techniques used. Ingredients used are, for instance, generally available USP grade commercial materials.

EXAMPLE

A formulation is prepared by adding purified water in an appropriate container, for example, in a beaker. Xylitol is then added with agitation. Glycerin vegetable is added to the mixture with agitation, followed by propylene glycol and flavoring agent. Once all components are well mixed, agitation is stopped, a 10% nicotine solution in propylene glycol is carefully added and the mixture agitated until well mixed. Table 1 summarizes exemplary weight ratios to be used in the formulation.

TABLE 1

| Material | Amount (wt %) (1 mg/dose) | Amount (wt %) (2 mg/dose) |
|---|---|---|
| Nicotine | 0.7% | 1.3% |
| Propylene glycol* | 41% | 35% |
| Glycerin | 28% | 26% |
| Xylitol | 1.3% | 2.6% |
| Flavor | 10% | 16% |
| Water | 19% | 19% |

*Total content in propylene glycol

Although the invention has been illustrated and described with respect to one or more implementations, equivalent alterations and modifications will occur to others skilled in the art upon the reading and understanding of this specification. In addition, while a particular feature of the invention may have been disclosed with respect to only one of several implementations, such feature may be combined with one or more other features of the other implementations as may be desired and advantageous for any given or particular application.

Accordingly, it is understood that the examples and embodiments described herein are for illustrative purposes only and that various modifications or changes in light thereof will be suggested to persons skilled in the art and are to be included within the spirit and purview of this application and scope of the appended claims. Any publication, document, patent, patent application or publication referred to herein should be construed as incorporated by reference each in their entirety for all purposes.

The invention claimed is:

1. A liquid formulation comprising nicotine, at least one lower alkyl diol and/or triol, a sugar alcohol and water, wherein the liquid formulation is free of ethanol, wherein the weight ratio of the sugar alcohol to nicotine is from about 1:1 to about 3:1.

2. The liquid formulation of claim 1, wherein the content in nicotine in the formulation ranges from about 0.2 wt % to about 2.5 wt %.

3. The liquid formulation of claim 2, wherein the content in nicotine in the formulation ranges from about 0.4 wt % to about 1.5 wt %.

4. The liquid formulation of claim 1, wherein the sugar alcohol is selected from maltitol, sorbitol, xylitol, erythritol, and isomalt.

5. The liquid formulation of claim 4, wherein the sugar alcohol is xylitol.

6. The liquid formulation of claim 1, wherein the content in sugar alcohol in the formulation ranges from about 0.5 w % to about 10 wt %.

7. The liquid formulation of claim 6, wherein the content in sugar alcohol in the formulation ranges from about 0.8 w % to about 5 wt %.

8. The liquid formulation of claim 1, wherein the weight ratio of sugar alcohol to nicotine is about 2:1.

9. The liquid formulation of claim 1, wherein said formulation comprises two or more lower alkyl diol, lower alkyl triol, or a combination thereof.

10. The liquid formulation of claim 1, wherein the lower alkyl diol and/or triol is selected from ethylene glycol, propylene glycol, and glycerol.

11. The liquid formulation of claim 1, wherein the total content in lower alkyl diol and/or triol in the formulation ranges from about 45 wt % to about 85 wt %.

12. The liquid formulation of claim 11, wherein the total content in lower alkyl diol and/or triol in the formulation ranges from about 55 wt % to about 75 wt %.

13. The liquid formulation of claim 1, wherein the lower alkyl diol and/or triol comprises propylene glycol and glycerol.

14. The liquid formulation of claim 13, wherein the lower alkyl diol and/or triol comprises propylene glycol and glycerol in a weight ratio of about 4:6 to about 8:2.

15. The liquid formulation of claim 1, further comprising a flavoring agent.

16. The liquid formulation of claim 15, wherein the content in the flavoring agent in the formulation is from about 3 wt % to about 20 wt %.

17. The liquid formulation of claim 1, wherein the content in water in the formulation is 30 wt % or lower.

18. The liquid formulation of claim 15, wherein the flavoring agent is selected from mint, grape, coffee, orange, and a combination thereof.

19. The liquid formulation of claim 17, wherein the content in water in the formulation is about 10 wt % to about 25 wt %.

20. Method for treating, reducing, or alleviating at least one tobacco withdrawal symptom in a subject in need thereof, comprising administering to said subject an effective amount of a liquid formulation as defined in claim 1.

21. The method of claim 20, wherein said liquid formulation is administered to the mouth cavity, for instance, in the form of an oral spray.

* * * * *